US012109339B2

(12) United States Patent
Kim

(10) Patent No.: US 12,109,339 B2
(45) Date of Patent: Oct. 8, 2024

(54) FLATULENCE CLEANING APPARATUS

(71) Applicant: Hong Min Kim, Toronto (CA)

(72) Inventor: Hong Min Kim, Toronto (CA)

( * ) Notice: Subject to any disclaimer, the term of this patent is extended or adjusted under 35 U.S.C. 154(b) by 788 days.

(21) Appl. No.: 16/974,174

(22) Filed: Nov. 3, 2020

(65) Prior Publication Data

US 2022/0133936 A1    May 5, 2022

(51) Int. Cl.
| | | |
|---|---|---|
| *B01D 53/22* | (2006.01) | |
| *A61L 9/014* | (2006.01) | |
| *A61L 9/14* | (2006.01) | |
| *B01D 53/04* | (2006.01) | |
| *B08B 3/08* | (2006.01) | |
| *B08B 5/04* | (2006.01) | |

(52) U.S. Cl.
CPC ............. *A61L 9/014* (2013.01); *A61L 9/14* (2013.01); *B01D 53/0454* (2013.01); *B08B 3/08* (2013.01); *B08B 5/04* (2013.01); *A61L 2209/111* (2013.01); *A61L 2209/134* (2013.01); *A61L 2209/22* (2013.01); *B01D 2253/102* (2013.01); *B01D 2257/302* (2013.01); *B01D 2257/90* (2013.01); *B01D 2257/91* (2013.01); *B01D 2259/45* (2013.01)

(58) Field of Classification Search
CPC ............. A61L 9/014; A61L 2209/111; A61L 2209/22; A61L 9/14; A61L 2209/134; B01D 2257/90; B01D 2259/45; B01D 2257/91; B01D 53/0454; B01D 2257/302; B01D 2253/102; B08B 3/08; B08B 5/04
See application file for complete search history.

(56) References Cited

U.S. PATENT DOCUMENTS

| | | | | |
|---|---|---|---|---|
| 2,280,838 A | * | 4/1942 | Murdock | E03B 9/20 |
| | | | | 137/305 |
| 2,927,561 A | * | 3/1960 | Eggers | F02M 25/028 |
| | | | | 180/335 |
| 3,744,216 A | * | 7/1973 | Halloran | A61L 9/22 |
| | | | | 55/315 |
| 4,536,198 A | * | 8/1985 | Strain | B01D 53/261 |
| | | | | 96/115 |
| 5,871,562 A | * | 2/1999 | Culoso | A61L 9/122 |
| | | | | 96/272 |
| 6,073,771 A | * | 6/2000 | Pressley | B65D 81/266 |
| | | | | 206/524.4 |
| 6,202,641 B1 | * | 3/2001 | Lazzaro | F24C 15/20 |
| | | | | 126/299 F |
| 6,585,791 B1 | * | 7/2003 | Garito | B01D 46/546 |
| | | | | 604/35 |

(Continued)

FOREIGN PATENT DOCUMENTS

EP        1946781 A1 *  7/2008  ............. A61L 2/10

*Primary Examiner* — Anthony R Shumate

(74) *Attorney, Agent, or Firm* — David W. Wong

(57) ABSTRACT

An apparatus is for cleaning flatulence of obnoxious odor, infectious virus and/or bacteria, and other contaminants. It can be mounted underneath a seat or bed provided with a flatulence collecting means. Flatulence is drawn through a series of chambers with charcoal provided in a first chamber for removing the obnoxious odor, copper wool provided in a second chamber having plurality of maze-like chambers for capturing and exterminating virus and/or bacteria; and a final chamber having sanitizing mist for eliminating contaminants.

7 Claims, 4 Drawing Sheets

(56) References Cited

U.S. PATENT DOCUMENTS

| | | | |
|---|---|---|---|
| 2010/0132144 A1* | 6/2010 | Rautray | A47L 17/08 15/104.93 |
| 2013/0042844 A1* | 2/2013 | Spix | F01M 13/023 123/573 |
| 2017/0245495 A1* | 8/2017 | Davis | A01N 49/00 |
| 2021/0121816 A1* | 4/2021 | Kim | B01D 46/0005 |
| 2022/0097878 A1* | 3/2022 | Mortimer | G07F 11/44 |
| 2022/0161189 A1* | 5/2022 | Shimada | C12M 23/36 |
| 2022/0282407 A1* | 9/2022 | Choo | D03D 15/41 |

* cited by examiner

FLATULENCE CLEANING APPARATUS

BACKGROUND OF THE INVENTION

1. Field of the Invention

This invention relates to an apparatus for de-odorizing, cleaning and sanitizing flatulence. The apparatus can be incorporated in a flatulence gathering device such as a seat or bed for collecting the flatulence from a person resting thereon to provide a clean air environment.

2. Background Art

Human passes obnoxious smelling gas or flatulence frequently. Flatulence generally contains 20 to 90% of nitrogen, 0 to 50% of hydrogen, 10 to 30% of oxygen, 0 to 10% of methane, and dimethyl sulfide and non-typical gases such as hydrogen sulfide ($H_2S$) which contributes largely to its obnoxious smell. Skatole and indole, and by-products of meat digestion is usually also included. The molecular signal of the hydrogen sulfide gas carries a number of signaling functions of the human gastrointestinal tract, and the flatulence may also carries fragments of any virus or bacteria from patients with viral or bacterial infections.

Sewage monitoring systems have employed a straining method to detect the level of presence of vitral fragments of COVID-19 virus in stools in sewage waste water for monitoring any changes of virus infection in a city or in any geographic region served by the waste treatment system. Thus, it is clear evidence that for a person infected with virus such as the Coronavirus, or other bacteria that cause diseases, the flatulence released by an infected person may also carry such harmful virus and/or bacteria which can cause transmission of the virus and/or bacteria to other people. Particularly in an indoor environment in which the flatulence with its obnoxious odor and any accompanying virus and/or bacteria may also be deposited on surfaces, for a long period of time so that the chances are very likely of the accompanying virus and/or bacteria and the obnoxious odor be inhaled by other people and the virus and/or bacteria be transmitted to other people coming into contact with the contaminated surfaces thus resulting in spread of the viral and/or bacterial infection causing the disease.

In U.S. Pat. No. 7,559,610 issued on Jul. 14, 2009 to the applicant of the present application, a seat is shown for collecting flatulence from a person sitting on the seat and the flatulence is passed through a filter for removing its obnoxious odor. The system shown in this prior art patent is effective in removing the obnoxious odor of the flatulence. However, it does not provide any function of cleaning and sanitizing the flatulence to eliminate any virus and/or bacteria and other contaminants that may be present in the flatulence.

SUMMARY OF THE INVENTION

It is the principal object of the present invention to provide an apparatus which can effectively not only remove the obnoxious odor of flatulence but also exterminate any virus and/or bacteria, and other contaminants that may be present in the flatulence.

It is another object of the present invention to provide an apparatus which can be easily incorporated in any flatulence collecting devices for cleaning the flatulence to provide a odor-free, virus-free and/or bacteria-free, and contaminants-free environment.

Briefly, the flatulence cleaning apparatus of the present invention comprises a system with main components contained in an enclosed casing which can be mounted underneath a chair, bed, and the like adjacent to a flatulence collecting device provided under the seat of the chair, or the mattress of the bed. The housing of the casing has an inlet port connected to the flatulence collecting device with a duct or tube. An inlet chamber in the housing is located adjacent to the inlet port. A temperature sensor is mounted in said inlet chamber or alternatively mounted at the flatulence collecting device. An odor removing chamber is located next to the inlet chamber which is filled with carbon particles operative for removing the obnoxious odor of the flatulence. A sensor chamber is located next to the odor removing chamber. A sulfur dioxide sensor and a inlet virus/bacteria sensor are mounted in a sensor chamber located next to the odor removing chamber. The temperature sensor, the sulfur dioxide sensor, and the virus/bacteria sensor are connected to a main control for operating various components of the flatulence cleaning device. An exterminating chamber is located next to the sensor chamber. A plurality of partition walls spaced from one another are located within the exterminating chamber in a staggered manner to form a plurality of maze-like chambers in the exterminating chamber. Neighboring maze-like chamber communicate with one another through gaps between opposite vertical side edges of neighboring partition walls spaced from opposite inside side wall of the housing. The maze-like chamber is filled with copper wool. A sanitizing chamber is provided at the exit end of the exterminating chamber. A injection nozzle is located in the sanitizing chamber for spraying a mist of sanitizing fluid onto the flatulence after it flows through the maze-like chambers. A blower fan is mounted adjacent to the outlet port for drawing the flatulence flowing through the device in a speed regulated by the main control. The de-odorized, virus/bacteria free, and contaminants-free clean air is released to the environment through the outlet port by the blower fan.

BRIEF DESCRIPTION OF THE DRAWINGS

Other objects and advantages of the present invention will become apparent from the following detailed description of the preferred embodiments thereof in connection with the accompanying drawings, in which.

DETAILED DESCRIPTION OF THE PREFERRED EMBODIMENTS

Figure 1:
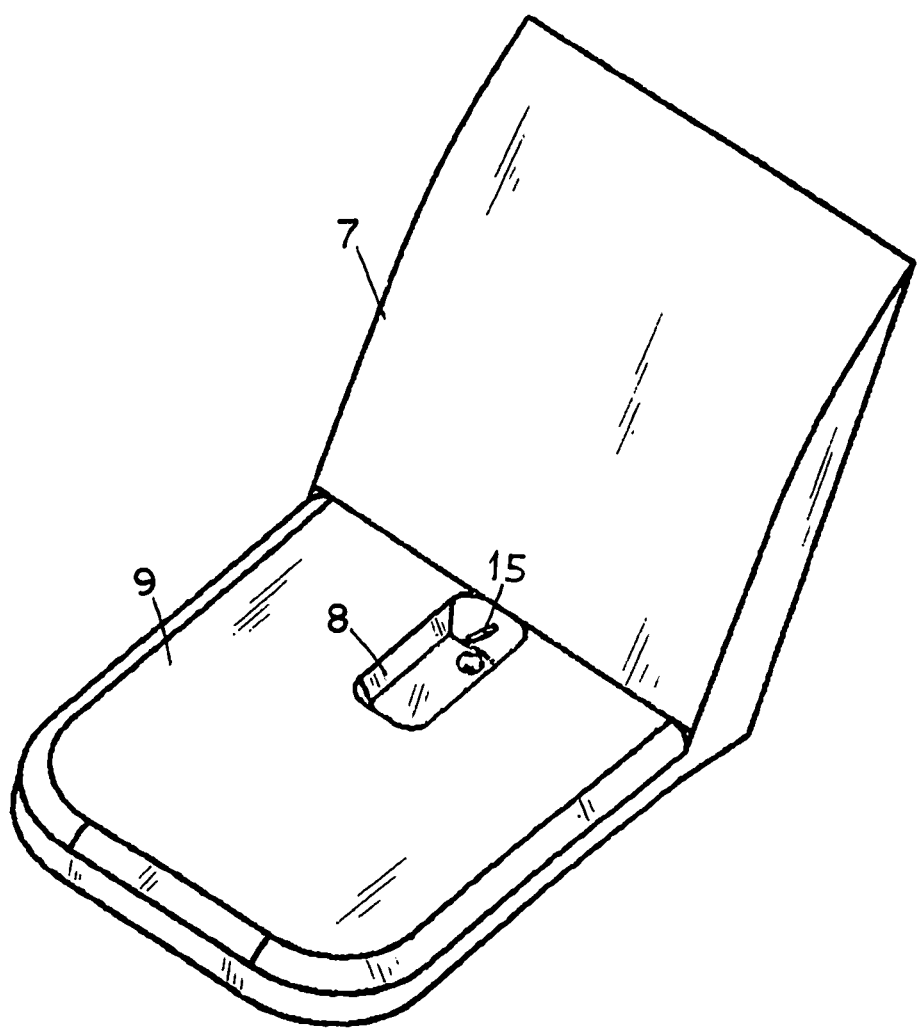
FIG. 1 is a perspective top and side elevation view of the seat portion of a chair having a flatulence collection well with a temperature sensor provided therein.
Figure 2:
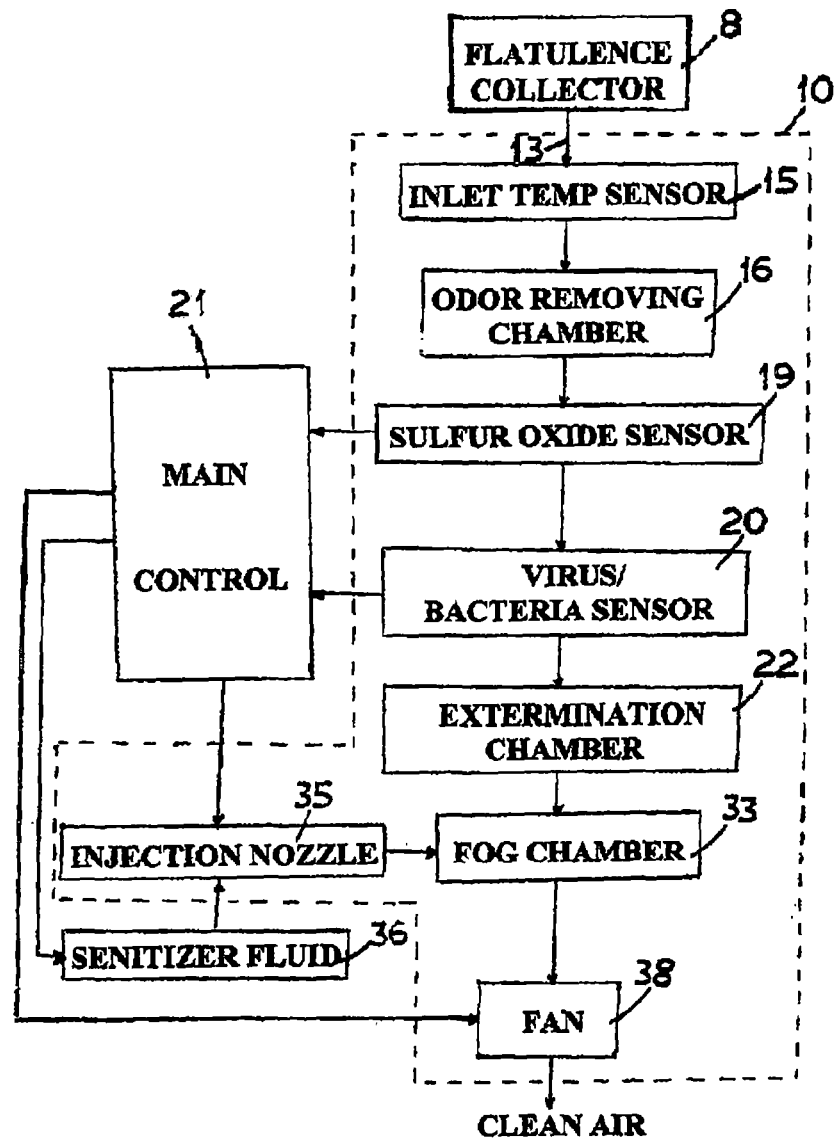
FIG. 2 is a schematic block diagram showing the system and operation of the apparatus of the present invention.
Figure 3:
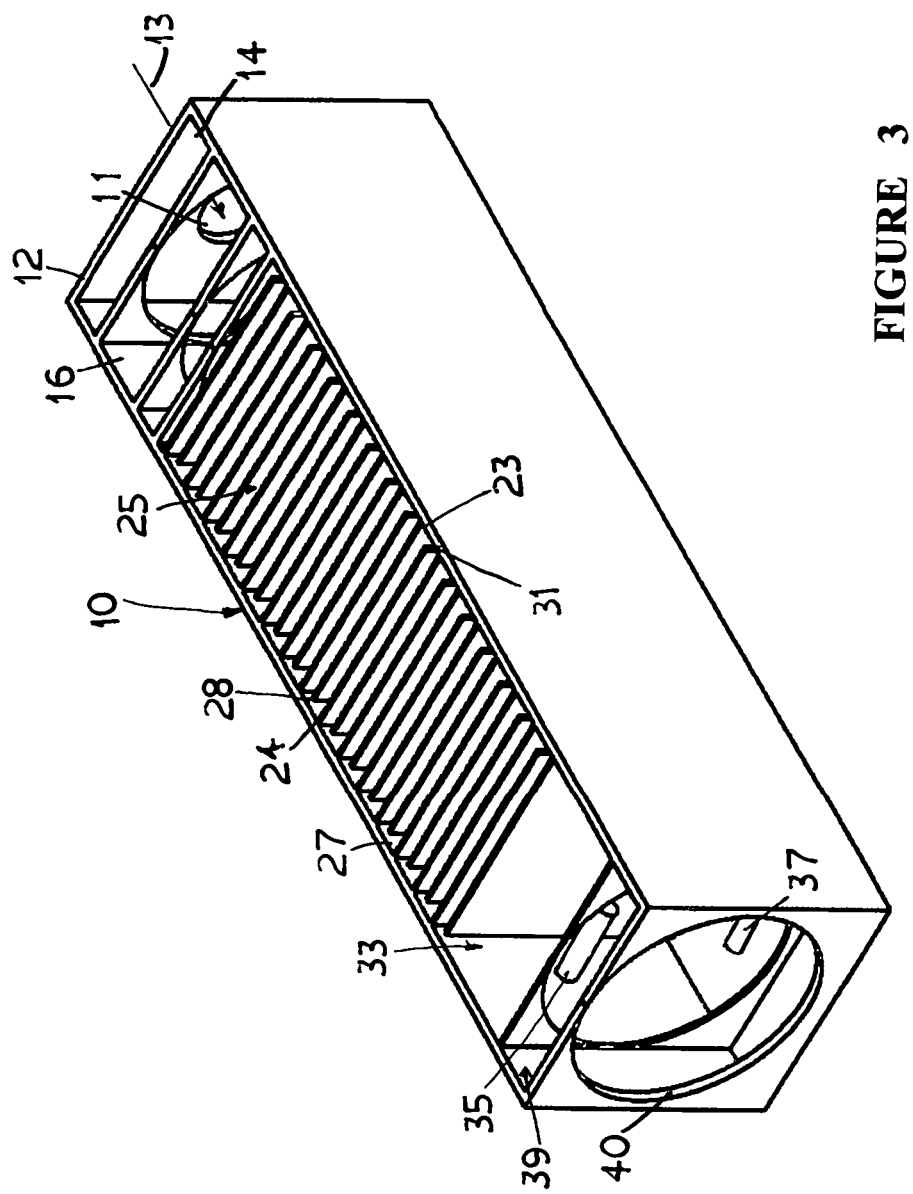
FIG. 3 is a perspective top and side elevation view of the apparatus with the top panel the casing removed to show the internal construction of the composite housing.
Figure 4:
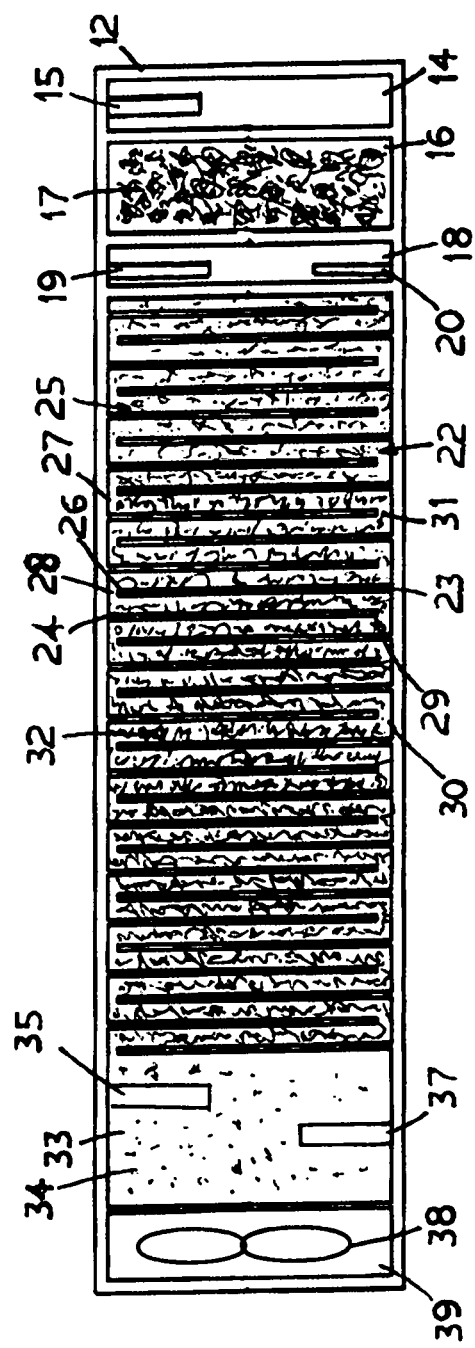
FIG. 4 is a perspective top elevation view of the apparatus with the top panel removed to show the location of various components therein.

The components of the apparatus of the present invention as shown in the schematic block diagram of FIG. 2 can be provided in a composite housing. The apparatus can be conveniently mounted under the seat portion of a chair or the mattress of a bed on which a person is resting. FIG. 1 shows an exemplary embodiment of a chair 7 having a flatulence collecting well 8 formed in its seat portion 9. The apparatus of the present invention can be mounted underneath the seat adjacent to the flatulence collecting well. As best shown in FIGS. 3 and 4, the composite housing 10 of the apparatus of the present invention has an inlet port 11 located at one end panel 12 for connecting to the flatulence collecting device by a duct or tube. The incoming flatulence 13 is received in an inlet chamber 14. A temperature sensor 15 is located in the inlet chamber 14 adjacent to the inlet port 11 to detect the incoming flatulence 13. The temperature sensor 15 is connected to aa main control unit 21 which may be physically located in the composite housing 10 or in a separate housing attached to the composite housing 10. The main control 21 upon receipt of the signal from the temperature sensor 15 will actuate or wake up the present device which is normally in a stand by stage so as to save the energy use of the device. Alternatively, the temperature sensor 15 may be located in the flatulence collecting device located at the seat or bed as shown in FIG. 1. The flatulence is then passed to an odor removing chamber 16 filled with carbon particles 17 for removing the obnoxious odor. After having de-odorized in the odor removing chamber 16, the gas is passed to a second sensor chamber 18 having a sulfur oxide sensor 19 and a virus/bacteria sensor 20 located therein. The sulfur oxide sensor 19 and the inlet virus/bacteria sensor 20 are connected to the main control unit 21 to determine the level of obnoxious sulfur oxide level and the amount of virus/bacteria contained in the flatulence. Subsequently, the flatulence is passed to an extermination chamber 22 having a plurality of staggered partition walls 23 and 24 spaced from one another to form plurality of maze-like chambers 25.

A vertical free side edge 26 of the partition wall 23 is spaced from the internal surface of the side wall 27 of the housing 10 to form a gap 28 therein and the opposite vertical free side edge 29 of the neighboring partition wall 24 is spaced from the opposite inside surface of the opposite side wall 30 of the housing 10 to form a gap 31 therein. Thus, the neighboring partition walls 23 and 24 are located in a staggered manner inside the extermination chamber 22 to form a plurality of maze-like chambers 25 with gaps 28 and 31 located at opposite sides of the extermination chamber 22. The neighboring maze-like chambers 25 communicate with one another through the gaps 28 and 31. The maze-like chambers 25 are filled with copper wool 32. The flatulence passes through the maze-like chambers 25 in a tortured zig zag manner and through the gaps 28 and 31 between the partition walls 23 and 24 to the side walls 27 and 30 such that any bacteria and/or virus in the flatulence will be captured and trapped in the copper wool 32. The copper wool 32 has a layer of copper oxide naturally formed on its surface. The copper oxide possesses biocidal properties to cause oxidative damage to virus/and bacteria captured on the copper wool and will result in desiccation and subsequent cell death of the bacteria and/or virus.

In a fog chamber 33 located at the end portion of the extermination chamber 22 the flatulence is further subjected to a sanitizing mist spray 34 provided by a spray nozzle 35 to ensure the removal of all possible contaminants in the flatulence. The sanitizing liquid of the spray 34 is supplied by a sanitizing liquid container 36 which is preferably physically separate from the housing 10 so as to facilitate convenient filling and replenishment of the sanitizing fluid. A fluid level sensor is provided in the sanitizing liquid container 36, and the fluid level container 36 is connected also to the main control 21 to monitor the amount of liquid in the sanitizing liquid container as well as to determine the amount of sanitizing mist spray 34 to be applied to the flatulence according to input signal received from the inlet virus/bacteria sensor 20. The complete removal of all bacteria and/or virus and contaminants is detected by an outlet virus/bacteria sensor 37 located also at the end of the extermination chamber 22. The second virus/bacteria sensor 37 is connected to the main control 21 which provides this determination. The flow rate of the flatulence through the apparatus is regulated by a blower fan 38 located in an outlet chamber 39 located adjacent to the outlet end of the housing 10. The main control 21 will adjust the speed of the blower fan 38 to regulate the flow speed of the flatulence through the apparatus according to the information received from the various sensors indicative of the amount of virus, bacteria, and contaminants in the flatulence. The clean gas, namely the flatulence devoid of obnoxious odor, virus/bacteria, and other contaminants, is released to the environment from the present apparatus through the outlet port 40.

What is claimed is:

1. A flatulence cleaning apparatus comprising:
a housing having an inlet port for receiving incoming flatulence and an outlet port for releasing clean air from said housing into surrounding environment;
an inlet chamber in said housing and located adjacent to said inlet port;
an odor removing chamber located next to said inlet chamber; said odor removing chamber being filled with carbon particles operative for removing obnoxious odor of said flatulence;
a sensor chamber located next to said odor removing chamber, a sulfur dioxide sensor and an inlet virus and bacteria sensor being connected to a main control;
an extermination chamber located next to said sensor chamber;
a plurality of partition walls spaced from one another and located within said extermination chamber, neighboring chambers in said extermination chamber communicating with one another through gaps between a vertical side edge of one partition wall and an adjacent first side wall of said housing, and between an opposite vertical edge of the neighboring partition wall and a second side wall opposite to said first side wall of said housing, said neighboring chambers being filled with copper wool;
a blower fan located in an outlet chamber of said housing adjacent to said outlet port and being operative for drawing the flatulence to flow in a regulated speed through said housing.

2. A flatulence cleaning apparatus according to claim 1 including an injection nozzle and an outlet bacteria sensor located in a fog chamber of said extermination chamber and adjacent to said outlet chamber, said injection nozzle being operative for injecting a mist of a sanitizing liquid onto said flatulence after said flatulence has flowed through said neighboring chambers for removing any remaining contaminants in said flatulence, said injection nozzle being regulated by said main control depending on input signal receiving from said inlet bacteria sensor.

3. A flatulence cleaning apparatus according to claim 2 including a sanitizing fluid container supplying said sanitizing liquid to said injection nozzle.

4. A flatulence cleaning apparatus according to claim 3 including a fluid level sensor provided in said sanitizing fluid container for monitoring amount of sanitizing fluid in said sanitizing fluid container.

5. A flatulence apparatus according to claim 2 including a temperature sensor located in said inlet chamber, said temperature sensor being connected to said main control operative for actuating said flatulence apparatus.

6. A flatulence cleaning apparatus according to claim 2 including a temperature sensor located in a flatulence collection device provided at a seat on which a person is resting and said flatulence collection device being connected to the inlet port of the cleaning apparatus by a flatulence conducting duct.

7. A flatulence cleaning apparatus comprising:
a housing having an inlet port for receiving incoming flatulence, and an outlet for releasing clean air from said housing into surrounding environment;
an inlet chamber in said housing and located adjacent to said inlet port;
a temperature sensor located in said inlet chamber, said temperature sensor being connected to a main control for controlling a plurality of operations of the flatulence cleaning apparatus, said temperature sensor being connected to a central control device for actuating the flatulence cleaning apparatus;
an odor removing chamber in said housing and located next to said inlet chamber, said odor removing chamber being filled with carbon particles operative for removing obnoxious odor of the flatulence flowing through said flatulence cleaning apparatus,
a sensor chamber located next to said odor removing chamber, a sulfur oxide sensor and an inlet virus and bacteria sensor located in said sensor chamber, said sulfur oxide sensor and said inlet virus and bacteria sensor being connected also to said main control;
an extermination chamber located next to said sensor chamber, and a plurality of partition walls spaced from one another being located within said extermination chamber in a staggered manner forming a plurality of consecutive neighboring chambers in said extermination chamber, said neighboring chambers communicating with one another through alternately located gaps formed between a vertical side edge of one partition wall and an adjacent first side wall of said housing, and similar gaps formed between an opposite vertical edge of the neighboring partition wall and a second side wall located opposite to said first side wall of said housing, said neighboring chambers being filled with copper wool;
a sanitizing chamber located at an exit end portion of said extermination chamber;
a sanitizing spray nozzle located in said sanitizing chamber and operative for spraying a mist of sanitizing fluid on the flatulence after passing through said copper wool, said sanitizing spray nozzle being connected to said main control operative for regulating said mist according to input signal received from said virus and bacteria sensor;
a blower fan located in an outlet chamber located next to said sanitizing chamber and adjacent to said outlet port, said blower fan being operative for drawing the flatulence to flow through said housing, said blower fan being connected to said main control for regulating said blower fan to operate at a regulated speed for removing the obnoxious odor of said flatulence.

\* \* \* \* \*